(12) United States Patent
Gill et al.

(10) Patent No.: US 6,918,762 B2
(45) Date of Patent: Jul. 19, 2005

(54) LIGHT-GENERATING INSTRUMENT (75) Inventors: Owen J. Gill, Southbury, CT (US);
Edward Robert Shellard, Orange, CA (US)

(73) Assignee: Kerr Corporation, Orange, CA (US)

( * ) Notice: Subject to any disclaimer, the term of this patent is extended or adjusted under 35 U.S.C. 154(b) by 87 days.

(21) Appl. No.: 10/393,572

(22) Filed: Mar. 21, 2003

(65) Prior Publication Data
US 2004/0185413 A1 Sep. 23, 2004

(51) Int. Cl.$^7$ .................. A61C 19/00; H01L 33/00
(52) U.S. Cl. .................. 433/29; 362/800; 362/804
(58) Field of Search ............... 433/29, 215; 606/1, 606/13, 16; 607/88; 362/800, 804, 119

(56) References Cited

U.S. PATENT DOCUMENTS

| 4,385,344 | A | 5/1983 | Gonser ................ 362/32 |
|---|---|---|---|
| 4,398,885 | A | 8/1983 | Loge et al. ........... 433/126 |
| 5,003,434 | A | 3/1991 | Gonser et al. ......... 362/32 |
| 5,233,283 | A | 8/1993 | Kennedy .............. 320/13 |
| 5,634,711 | A | 6/1997 | Kennedy et al. |
| 6,200,134 | B1 * | 3/2001 | Kovac et al. .......... 433/29 |
| 6,331,111 | B1 | 12/2001 | Cao ................. 433/29 |
| 6,419,483 | B1 | 7/2002 | Adam et al. .......... 433/29 |
| 6,439,888 | B1 | 8/2002 | Boutoussov et al. .... 433/215 |
| 6,468,077 | B1 | 10/2002 | Melikechi et al. ..... 433/29 |
| 6,692,251 | B1 * | 2/2004 | Logan et al. ......... 433/29 |
| 2002/0014864 | A1 | 2/2002 | Gemunder et al. ...... 315/291 |
| 2002/0051367 | A1 | 5/2002 | Hooker et al. ........ 362/551 |
| 2002/0133970 | A1 | 9/2002 | Gordon et al. |
| 2003/0015667 | A1 | 1/2003 | MacDougald et al. |

FOREIGN PATENT DOCUMENTS

| EP | 1103232 A1 | 5/2001 |
|---|---|---|
| EP | 1090607 A1 | 11/2001 |
| EP | 1090608 A1 | 11/2001 |
| WO | WO 99/16136 * | 4/1999 |
| WO | WO 02/080808 A1 | 10/2002 |

* cited by examiner

Primary Examiner—Ralph A. Lewis
(74) Attorney, Agent, or Firm—Wood, Herron & Evans, L.L.P.

(57) ABSTRACT

The invention relates to light-generating instruments, which are small, compact and convenient to use. More particularly, the light-generating instruments are generally powered by air, electricity, or light provided by the operating unit, such as the dental chair. Air, electricity, and light provided by the dentist's chair allow for convenience to the dentist while eliminating potential risks and hazards associated with use of an electrical cord to power the instrument.

24 Claims, 4 Drawing Sheets

FIG. 5

LIGHT-GENERATING INSTRUMENT

FIELD OF THE INVENTION

The present invention generally relates to a light-generating instrument and method for curing light-curable compounds. More particularly, the invention provides a power system for the generation of light particularly useful for curing light-curable dental adhesives.

BACKGROUND OF THE INVENTION

Light-curable compounds, such as adhesives and bonding or filling compounds, are widely used to attach objects to surfaces or to fill gaps or other openings. Such curable compounds are generally available in a semi-solid state and are manipulated and positioned on the surface or in the gap as desired to be hardened or cured into a more solid state. Curing or hardening is generally a chemical polymerization process, which is promoted and driven by various curing conditions and factors. For example, a semi-solid compound or component thereof, maybe cured by exposure to air or to energy, such as heat or light energy.

Today, most adhesive and filling compounds are cured by exposure to light energy, particularly visible or ultraviolet light energy. The light-curing process involves directing a beam of light at a specific wavelength or band of wavelengths onto a semi-solid light-curable compound to cure the compound. Such a compound typically includes light-sensitive, chemical components, which, when exposed to light at the specific wavelength, generally polymerize to harden the compound to bond, fill, or coat the work surface.

Light-curable compounds are particularly widely used in dental procedures. Dentists use light-curable dental compounds for dental repairs in a variety of tooth related applications including use as a base, a liner, a coating, a surface seal, a filling for caries and cavities, and a bonding material to secure crowns, orthodontic appliances or other dental structures to a tooth surface. Generally, visible light in the blue range of the light spectrum will be sufficient to cure most commonly used dental compounds. Once cured, such a dental compound may function, for example, to reduce further tooth decay, to provide bonds for dental structures, or to provide additional structural support to a tooth. Generally, curing is effected by various instruments or devices capable of generating the curing light, for example, a beam of blue visible light, and directing this light onto a light-curable compound manipulated on the surface of a tooth. The curing light either penetrates into the compound layer on the tooth surface for complete curing or initiates a curing reaction near the surface of a compound that propagates into the compound to cure it. The duration of the exposure to light for proper curing of the compound layer depends upon the light-curable compound itself, the thickness of the compound layer, and particularly, the power and characteristics of the light emitted from the light-generating instrument. For example, curing a compound to provide a thin tooth surface coating or veneer might require less light energy, while curing a compound to provide a thicker, deeper filling for gaps, such as caries and cavities, might require a greater amount of light energy generally provided by a stronger, more powerful light-emitting device, an increase in light intensity, or longer curing times.

There are many different forms of light-generating instruments available to the operator, such as a dentist, for curing applications. A number of these light-generating instruments are powered electrically by energy sources external to the instrument. For instance, U.S. Pat. No. 4,398,885 discloses a dental handpiece for use in dental applications. The handpiece may be used as a light source provided by a bulb. The bulb in the handpiece is powered electrically by two pins at the end of the handpiece, which must be plugged into a connecting electrical socket, typically in the wall of the operator's office.

U.S. Pat. No. 4,385,344 discloses a light source with a tungsten halogen lamp used to cure light-curable compounds, particularly for use in dental applications. Here, the light source is connected electrically through electrical leads or circuit leads that must be plugged into a separate power supply unit.

U.S. Pat. No. 5,003,434 discloses a hand-held spot source of illumination suited for use by health professionals including dentists. This hand-held unit is electrically powered by electrical leads that must be plugged into an electrical source external to the unit itself, typically an outlet in the wall of the office in which the instrument is used.

A significant drawback in the use of such light-generating instruments is that the source of electrical power is the inconvenience of connecting the instrument to an electrical outlet and the inconveniences of the electrical cables needed to deliver power to the curing instruments. Battery operated instruments have been proposed, but the weight of batteries needed to operate and cool conventional curing instruments renders many of them inconvenient.

Thus, there is a need to provide a light-generating instrument that is effective, is convenient to use and operate and is low in cost.

SUMMARY OF THE INVENTION

Accordingly, an objective of the invention is to provide a light-generating instrument that is energy efficient, easy to use, and conveniently powered.

A further objective of the invention is to provide a light-generating curing instrument that is easy to handle and is light in weight while providing ample operating power. A particular objective of the invention is to provide a light-generating curing-light gun that is convenient for dental uses.

Another objective of the invention is to provide a light-generating instrument powered by energy sources otherwise present in the operator's equipment. A more particular objective of the invention is to provide a dental curing-light gun that is powered by energy sources present or accessible to a dental chair.

According to the principles of the present invention, a light-generating curing instrument is provided that derives power from sources convenient to the operator. According to various embodiments of the invention, a curing-light instrument is provided that is particularly useful for dental purposes, that is light in weight, and derives power to operate, or to store for future operation, from sources available at a dental treatment site.

According to described embodiments of the invention, a curing-light gun is provided that derives power from sources on or in the vicinity of a dental chair. One embodiment of the invention uses energy derived from air pressure or vacuum supply connections on a dental chair to generate electrical power to operate a curing-light generator, while preferably also providing cooling airflow to cool the light-generating components. Another embodiment of the invention uses electrical power from the dental chair to operate the light-generating components, while preferably also using air-flow or electrical power to generate airflow to cool the light-generating components. Still another embodiment uses ambient light at the dental treatment site to recharge storage cells in the instrument to a level needed to operate the instrument. Further embodiments use minimal electrical power from the site to operate the curing light while using airflow from the site for cooling.

The concepts discussed above are enhanced and rendered particularly effective by the use of highly energy efficient light-generating components, particularly light-emitting diodes and diode arrays as described in copending U.S. patent application Ser. No. 10/215,210, filed Aug. 8, 2002 by Owen Gill, et al. entitled CURING LIGHT INSTRUMENT, hereby expressly incorporated herein by reference.

The invention is more particularly directed to a dental curing-light-generating instrument, which derives power from the dentist's chair, of which various embodiments are illustrated and described.

The invention provides a curing gun that is convenient, lightweight, and does not require frequent charging of the power supply. The invention further provides a curing-light generating instrument that utilizes an LED for light generation and maintains low, stable operating temperature for efficient operation and long life of the LED.

BRIEF DESCRIPTION OF THE DRAWINGS

The foregoing and other objects, features, and advantages of the invention should become apparent in light of the following description when taken in conjunction with the accompanying drawings, in which.

DETAILED DESCRIPTION OF THE INVENTION

Figure 5:
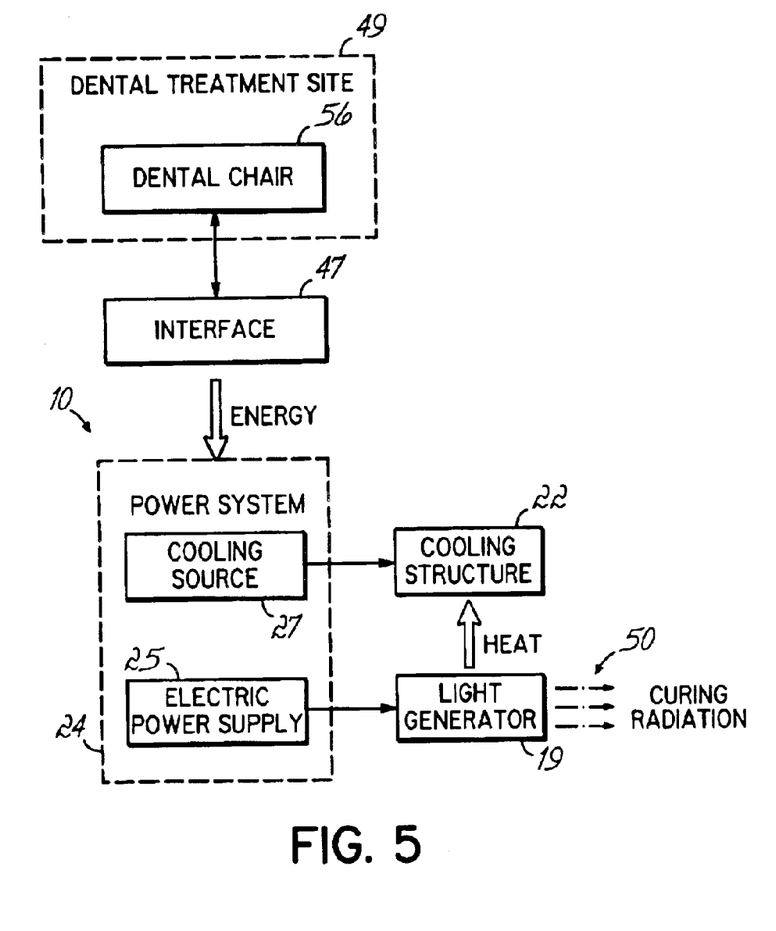
FIG. 5 is a diagrammatic representation of certain embodiments of a dental light-curing gun for use in a dental treatment site according to principles of the present invention.
Figure 6:
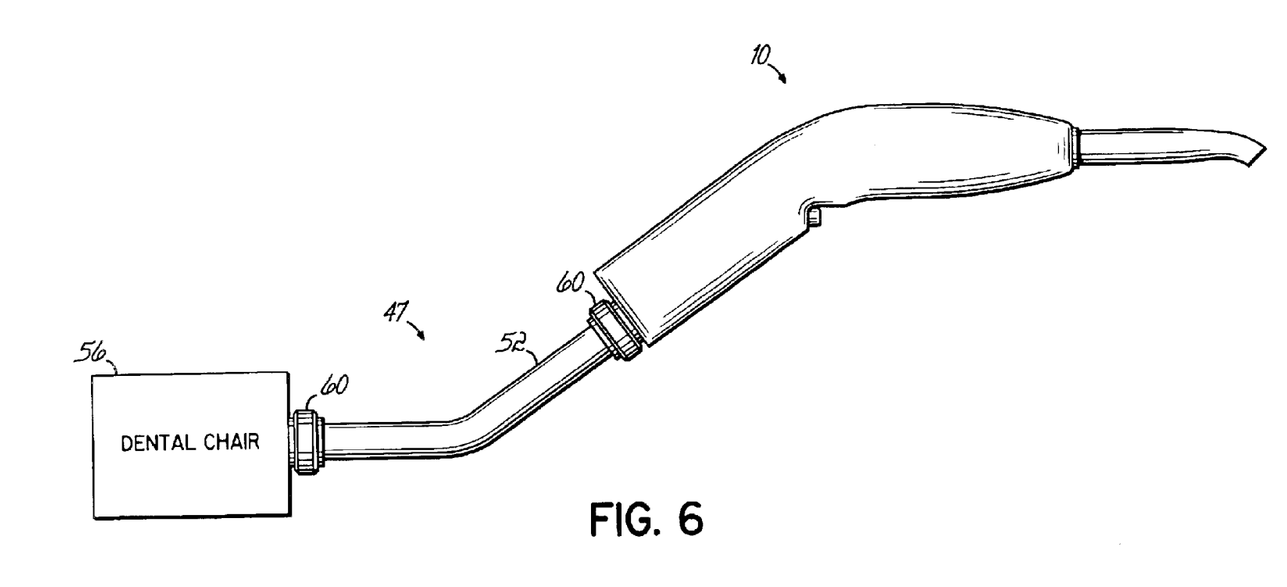
FIG. 6 is a perspective view of a light-curing gun connected to a dental chair according to an embodiment of the present invention.
Figure 7A:
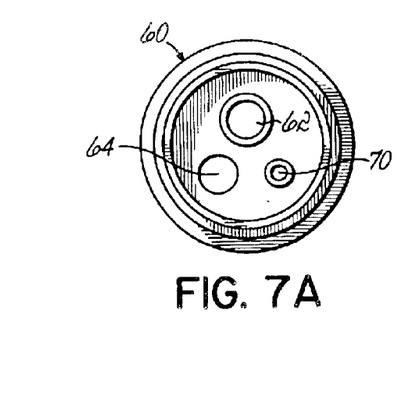
FIG. 7A is a cross-sectional view of a connector, according to an embodiment of the present invention.
Figure 7B:
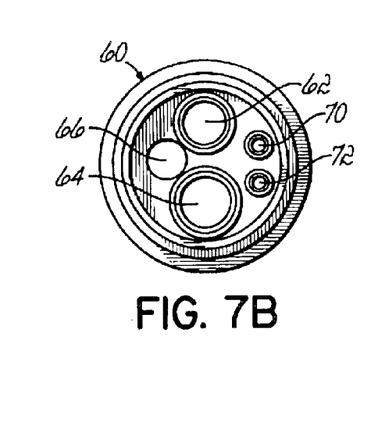
FIG. 7B is a cross-sectional view of a connector, according to another embodiment of the present invention.
Figure 7C:
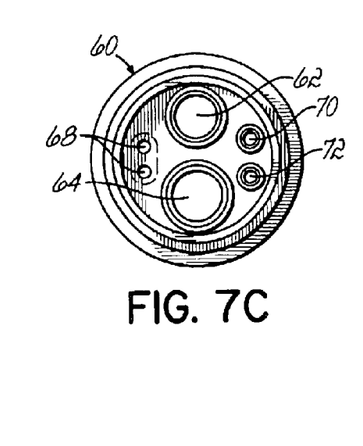
FIG. 7C is a cross-sectional view of a connector, according to a further embodiment of the present invention.

FIGS. 1–4 illustrate embodiments of light-generating instruments 10 used for curing light-curable compounds, and in particular, dental light-curable compounds. Each embodiment of the light-generating instrument 10 generally comprises a light generator 19 and a power system 24, as depicted in the diagram of FIG. 5. The alternative embodiments include additional physical components, some of which are illustrated in FIGS. 1–4 and discussed in greater detail below. The power system 24 includes a power supply 25 that supplies electrical energy to operate the light generator 19 and a cooling source 27 to supply cooling fluid, such as air, that cools the light generator 19. The energy and cooling fluid may be transferred to power system 24 through an interface 47 from a dental chair 56 in a dental treatment site 49. FIG. 6 illustrates an embodiment having the dental chair 56 interfaced via connectors 60 to instrument 10 to provide cooling air and/or an energy stimulus, such as air flow, light, and/or electricity, for powering instrument 10. FIGS. 7A–C illustrate exemplary embodiments of the connector 60 shown in FIG. 6.

The light-generating instrument 10 comprises a housing 11 to house components for supporting the generation of curing light. Housing 11 may be any shape, but is preferably a gun-shaped or a tubular-shaped structure having a proximal end 12 and a distal end 13. The housing 11 is preferably configured to allow external air to flow through the housing 11, for example, via an air inlet 15 to an air outlet 16 in housing 11. The housing 11 is composed of any suitable materials. Particularly useful are lightweight compact fireproof materials, such as plastic, typically used in the art.

The light generator 19 is located inside housing 11 and includes a light device 18 to generate a beam of light 50 radiated onto a light-curable compound (not shown) to cure the compound. The light device 18 is typically mounted onto a substrate 20. Substrate 20 is preferably housed in the distal end 13 and supported by the housing 11. For example, support may be provided by direct attachment to housing 11 or indirect attachment through an intermediary cooling structure 22, such as a heat sink. The substrate 20 primarily functions to mount and cool the light device 18. The shape of the substrate 20 may vary and may depend upon the design and space available in instrument 10.

The light device 18 may be any conventional light-emitting device used for, or capable of, generating light in wavelengths and intensities sufficient to cure light-curable compounds. Conventional light devices typically include halogen bulbs or other such radiant energy sources. Preferred for use with the present invention are, however, devices such as light-emitting diodes, typically known and referred to hereinafter as LEDs. The use of LED light-generating devices is described in U.S. patent application Ser. No. 10/215,210 referred to above.

A particularly useful and efficient light device 18 is one, which comprises light-emitting diodes which generate a beam of light 50 for transmission out of the distal end 13 of the housing 11. The LEDs are typically made of light-generating semiconducting material. Such LEDs are essentially unpackaged semiconductor junctions for generating the desired light. Each LED requires approximately 4–5 volts of DC bias electricity. Individual LEDs may generally be any shape, and typically measure approximately 1 mm on a side, or 1 $mm^2$ in area.

It is advantageous to use a light device 18 comprising a plurality of LEDs arranged in an array, which collectively, provides a very high density of light suitable in wavelength and intensity to effectively cure a light-curable compound. The array of LEDs, by virtue of each LED being so small, collectively provide an overall smaller surface area than conventional LEDs. Each individual LED may be arranged or spaced as desired to form the array. The array may vary in shape or size, as necessary, depending upon the size and shape of the substrate 20 on which they are mounted. Other factors influencing the size and shape of the array generally include light requirements of the instrument in general and the cooling system available. In addition, the number of LEDs may increase depending upon the type of compound to be cured and the types of dental applications for which the instrument 10 is used. For example, curing a deep filling or thicker surface coating may require stronger radiation, which may be provided by a larger number of LEDs.

Radiated power levels of at least approximately 200 $mW/cm^2$ or greater are generally necessary for curing the available dental compounds. The light-generating instruments described above and below may be configured for use in curing dental compounds and are particularly useful for such purposes.

Substrate 20 generally comprises thermally conductive materials to dissipate heat generated by light device 18. For example, the substrate 20 may be formed of a ceramic material, such as alumina, or silica, to provide the necessary cooling for the light device as it operates. Thermally coupling the substrate 20 to heat sink or other cooling structure 22 is beneficial for further cooling purposes. Additional cooling devices, such as a fan, may be strategically housed for directing cool air towards the heat sink 22 and/or the light device 18 to provide further cooling. Advantageously, the light device 18 and heat sink 22 are also cooled by air circulating within the housing 11.

The heat sink 22 is thermally coupled to the light device 18 to assist in cooling the instrument 10. More particularly, light device 18 is mounted on a substrate 20, which is thermally coupled to the heat sink 22. The heat sink 22 typically has fingers or fins 23 which increase the surface area by which a maximal amount of heat is dissipated. The housing 11 is accordingly configured to provide air into the instrument 10 through air inlet 15 proximate the heat sink 22 and proximate the light device 18 so as to flow across the fins 23 to provide cooling and dissipation of the heat from both the heat sink 22 and the light device 18.

The light-generating instrument 10 may further comprise a light-transmitting device such as a light guide 44. Light guide 44 typically has a proximal end 45 and a distal end 46. The proximal end 45 of the light guide 44 is generally configured to interface and fit to the distal end 13 of the housing 11. Light guide 44 may generally be any shape effective to transmit the emitted light onto a light-curable compound. Preferably, the shape of the light guide 44 is adapted for convenience of use depending upon the work surface. For instance, the light guide 44 may have a distal end 46 tapered and narrowed to better reach low lying and smaller surfaces, to provide effective curing, minimal oral tissue exposure, and convenience in curing a compound on a tooth in a patient's mouth. Suitable light guides 44 may be commercially available in a variety of different sizes and shapes, for example, in diameters of 8 mm, 11 mm, and 13 mm, respectively. As shown, the light guide 38 has a relatively uniform diameter from the proximal end 45 through the distal end 46. Preferably, the distal end 46 is tapered to the extent necessary to effectively transfer all of the light directly onto the light-curable compound.

Figure 1:
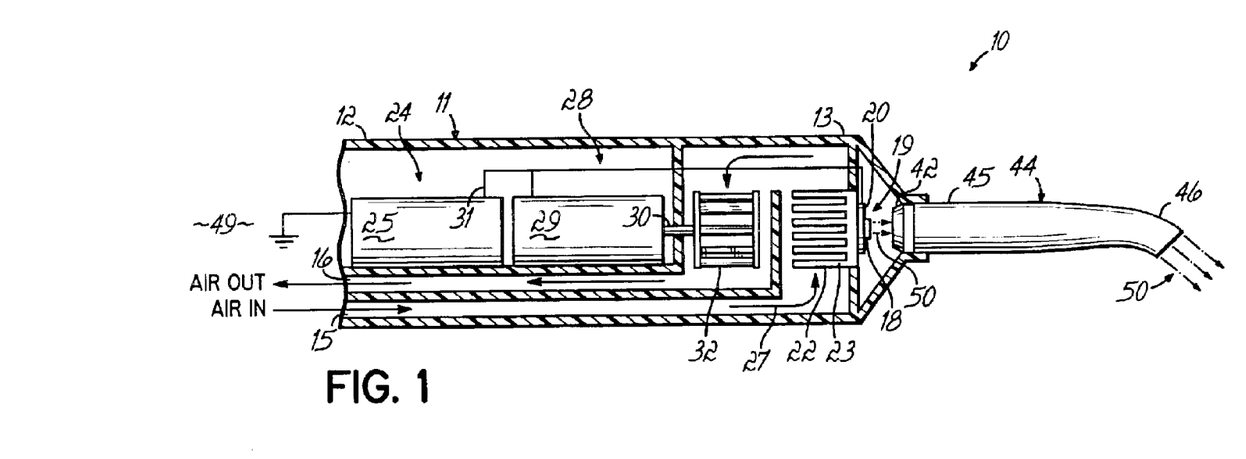
FIG. 1 is a cross-sectional view of a light-generating instrument, according to an embodiment of the present invention, having an air driven energy converting system to power a light device and cool the light device.

Generally, the light guide 44 is comprised of any components capable of effectively transmitting light without a decrease in light intensity. For instance, one embodiment of the invention utilizes a light guide 44 comprising a plurality of optical fibers (for example, approximately 5000 fibers), which are operably fused together into a single light guide or light pipe type structure to transmit the light 50. As shown in FIG. 1, the beam of light 50 is received by the proximal end 45 of light guide 44, also referred to as the receiving end, and transmitted out of the distal end 46 of light guide 44, also referred to as the transmission end. Proximal end 45 is generally removably secured to the distal end 13 of housing 11. Conventional securing means are suitable. For instance, proximal end 45 may be screwed into and out of the distal end 13 of housing 11. Conventional light guides known in the art are suitable for the present invention.

As FIGS. 1–4 illustrate further, a lens 42 may be positioned between the light device 18 and the receiving end 45 of the light guide 44. The lens 42 is typically used to direct or focus the light 50 emitted from the light device 18 into the receiving end 45 of the light guide 44. Conventional lens 42 or light focusing devices may be used.

The power system 24 for the instruments 10 is configured to reduce the need for heavy batteries while still providing a convenient and flexible curing instrument. Power is consumed by the light generator 19, which results in heating of the device, which adversely affects its efficiency and the control of its output of curing light. The preferred LED light generators consume less power, but are particularly sensitive to excessive heat. Cooling systems that provide fans and cooling fluid flow in the curing instruments add weight to the instrument, and in addition consume additional power, which, in turn, increases the need for heavy batteries while shortening battery life. The power system 24 is likewise configured to reduce the need for and the burdens of such cooling systems.

In particular, the light-generating instrument 10 has a power system 24 responsible for providing the necessary power to the light device 18 to generate light 50. As shown in FIG. 1, the power system 24 includes a power supply 25 to provide the power to the light device 18. The power supply 25 in the embodiment of FIG. 1 may include a rechargeable battery, which provides DC current to the light device 18. The power supply 25 is generally connected electrically to the light device 18 to activate the light device 18 via a connector 31 through a regulator circuit (not shown).

In the embodiment of FIG. 1, the light-generating instrument 10 comprises an energy converting device or system 28 to convert energy present in a flow of air into a form of energy usable by the light device 18. More specifically, the energy converting system 28 includes a DC generator 29 and a turbine 32 that is capable of converting airflow energy, or energy derived from the velocity of air, into mechanical energy for turning a shaft 30 of the generator to produce electrical energy. The electrical energy is stored either in the battery 25 or, as needed, is delivered by the power system 24 to power the light device 18. The energy converting system 28 is activated by a flow of air entering the housing 11 via the air inlet 15, across the turbine 32 and to the outlet 16. The air may be supplied by suitable means, such as from a dental chair, into the air inlet 15.

FIG. 1 illustrates a configuration wherein the air flows into the housing 11 via an air inlet 15 located in the proximal end 12 of housing 11. The housing 11 generally has a design such that air can flow through the housing 11 and out an air outlet 16 which, in FIG. 1, is also located in the proximal end 12 of housing 11. Either or both of the proximal end 12 and distal end 13 of the housing 11 may be vented for purposes of dissipating heat generated by the light device 18, preferably the end which houses the light device 18.

In certain embodiments of the invention, the cooling fluid source 27 is external to the curing instrument 10 at the site 49 of the curing operation. Such a source 27 may, for example and with reference to FIG. 5, be from the operator's chair, such as a dental chair 56, at a site 49, which is the site of dental treatment, e.g., a dentist's office. A dental chair is typically equipped with an ample air supply system. Air connections to the dental chair may be made by either connecting the inlet 15 to an air supply port in a dental chair, or by connecting the outlet 16 to a vacuum or exhaust port on a dental chair, or both (FIG. 6). As illustrated in FIG. 1, in the energy converting system 28, generator 29 is interfaced by connector 30 with the turbine 32. The turbine 32 spins as a result of the airflow from the air inlet 15 to generate energy, which is transferred to generator 29 through connector 30. Generator 29 then converts this energy into electrical energy and transfers it via the electrical connector 31 to the power system 24 and in particular to power supply 25. Power supply 25 then electrically feeds the energy to the light device 18 to generate light 50 to cure a compound. Further embodiments, illustrated in the figures and described below, include different modes of supplying power to actuate the light device 18 to cure a light-curable compound.

Figure 2:
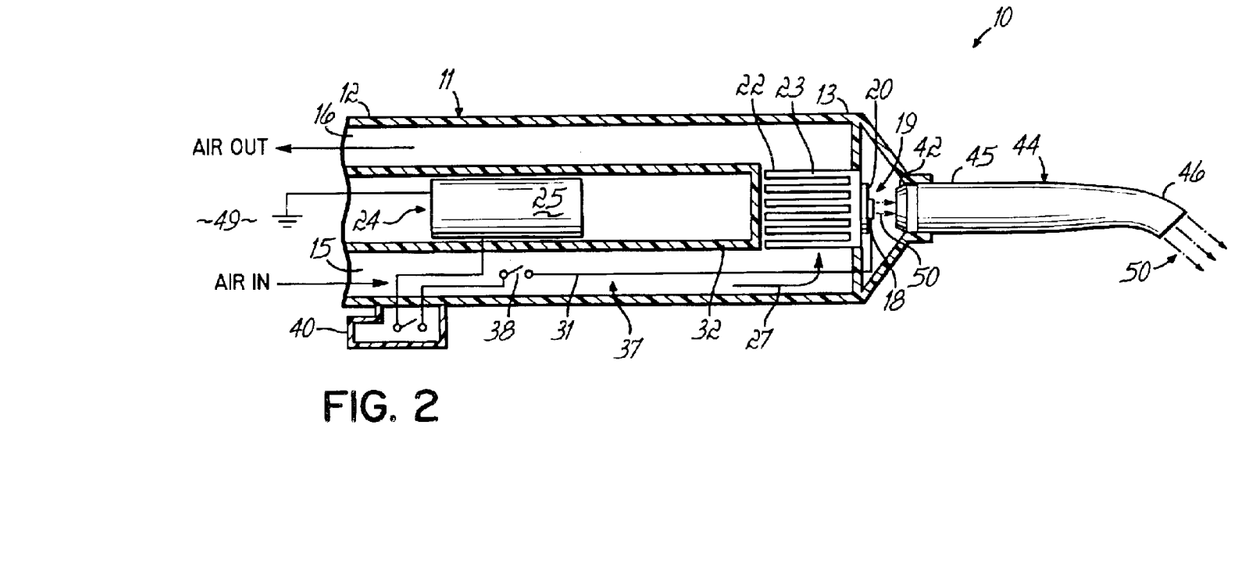
FIG. 2 is a cross-sectional view of a light-generating instrument, according to a further embodiment of the present invention, having an air-responsive switching circuit to activate the power to a light device and cool the light device.

FIG. 2 illustrates an embodiment of the invention wherein the light-generating instrument 10 comprises a power system 24 that includes an air-flow activated switching circuit 37 by which air from a dental chair controls an air-actuated switch or air-flow sensor 38 for powering the light device 18. The air from the dental chair also serves to cool the heat source 18 during operation. The switch 38 responds to the presence of cooling airflow to activate the light device 18 thereby preventing operation of the light-generating instrument 10 unless it is being cooled. The air-actuated switch or sensor 38 may be connected in series with a trigger switch 40 that allows the dentist to turn the curing light on and off at will, provided the air flow is established to close switch 38. Generally, the power system 24 is electrically coupled to the switching circuit 37. Alternatively, switch 38 may be responsive to changes in pressure. For example, switch 38 may be a pressure switch that responds to a pressure gradient from the inlet 15 to the outlet 16 would be effective.

For example, as shown, housing 11 may be configured to provide full exposure of switching circuit 37 to the air flowing within the housing 11. A flow of air through air inlet 15 of housing 11 primarily drives and causes the switching circuit 37 to operate. Airflow sensor 38, once activated in response to an airflow, enables the operator to trigger the switch 40 to connect the power supply 24 to the light device 18 to supply power for generating light to cure a light-curable compound. The airflow sensor 38 may be any conventional airflow sensor device, preferably one small, compact, and sensitive to even the slightest changes in airflow. Switch 40 is preferably a push and hold button or trigger-like lever that remains closed while the button is pushed. The embodiment shown in FIG. 2 is a portable light-generating instrument 10 in that the power system 24 comprises a power supply battery 25 electrically connected to the switching circuit 37. Switch 40 activates power system 24 to deliver electrical power to the light device 18.

The instrument 10 may also include a power supply control unit or a conditioning circuit (not shown) connected electrically to the power system 24. The conditioning circuit is generally located inside housing 11 and electrically coupled to the light device 18. Such a conditioning circuit conditions or regulates the electrical power or energy delivered to the light device 18, thereby allowing the operator to control or condition the precise amount of curing-light radiation required to cure a light-curable compound. The conditioning circuit is typically connected in a series with the lead 31 and the related components, such as switch 40 and the energy converting device 28 (FIGS. 1 and 3), to allow the operator to regulate the electricity generated from the power supply 25 to power the light device 18.

Figure 3:
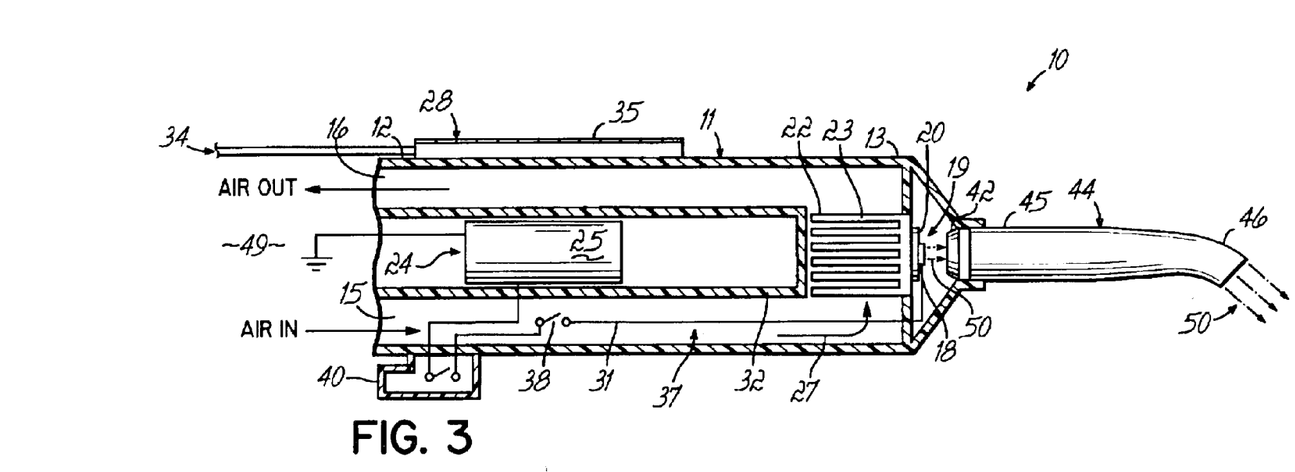
FIG. 3 is a cross-sectional view of a light-generating instrument, according to another embodiment of the present invention, having an energy converting device which absorbs light energy supplied from a dental chair to use to power a light device, and using air from the dental chair to cool the light device.

FIG. 3 illustrates another embodiment of the light-generating instrument 10 comprising an energy-converting device 28, which converts light energy to electrical energy to power the light device 18. As in the embodiments described above, external air from the site 49 is used for cooling, so that electrical energy is only needed for the light device 18, which, if an LED, has minimal power requirements.

The energy-converting device 28 may comprise at least one photocell 35 to absorb light energy from the environment or as otherwise supplied. The photocell 35 may be any conventional light absorbing photocell, such as a solar cell and the like. It is advantageous and efficient to provide the light-generating instrument 10 with a plurality of photocells 35. The photocells 35 may be arranged in a manner to efficiently and collectively absorb light energy. For example, the photocells 35 may be arranged in a linear array as shown. Photocells 35 may be located in the housing 11 or immediately exterior to the housing 11 provided they are located so as to maximize exposure to and absorption of visible light.

The source of visible light may be any suitable source, such as light immediately external the light generating instrument 10. Alternatively, the source of visible light may be provided by the operating unit. A provided light source, such as an optical light fiber 34 extending from the source and coupling to or feeding into the housing 11, has the advantage of controlling and timing the providing of visible light to charge, store, and power the photocells 35. In one embodiment, the source of visible light is a dental chair coupled to the housing 11 via a connector port 66 through which an optic fiber 34 feeds into the energy-converting device 28 to provide visible light to the photocells 35 (FIG. 7B). The photocell 35 absorbs light and converts the light energy into usable electrical energy to power the light device 18. The energy-converting device 28 is electrically coupled to the light device 18 to provide energy sufficient to generate light 50. Alternatively, the energy-converting device 28 may be positioned inside the housing 11 towards the proximal end 12.

The embodiment illustrated in FIG. 3 also includes a housing 11 having a proximal end 12 and a distal end 13 supporting a substrate 20. The housing 11 also has an air inlet 15 and an air outlet 16 to allow air to flow within the housing 11 when desired. The light device 18 is mounted to the substrate 20 to emit light 50 into the light guide 44 to transmit the light 50 onto a light-curable compound (not shown). The light device 18 is cooled by conductive heat transfer to the substrate 20 and the thermally coupled heat sink 22. The heat sink 22, in turn, is cooled by an air flow flowing into the air inlet 15 and out the air outlet 16 of the light-generating instrument 10. This embodiment also comprises a switching circuit 37 including an airflow sensor 38 and a switch 40 activated by an airflow from a source of air, such as that in a dental chair.

Figure 4:
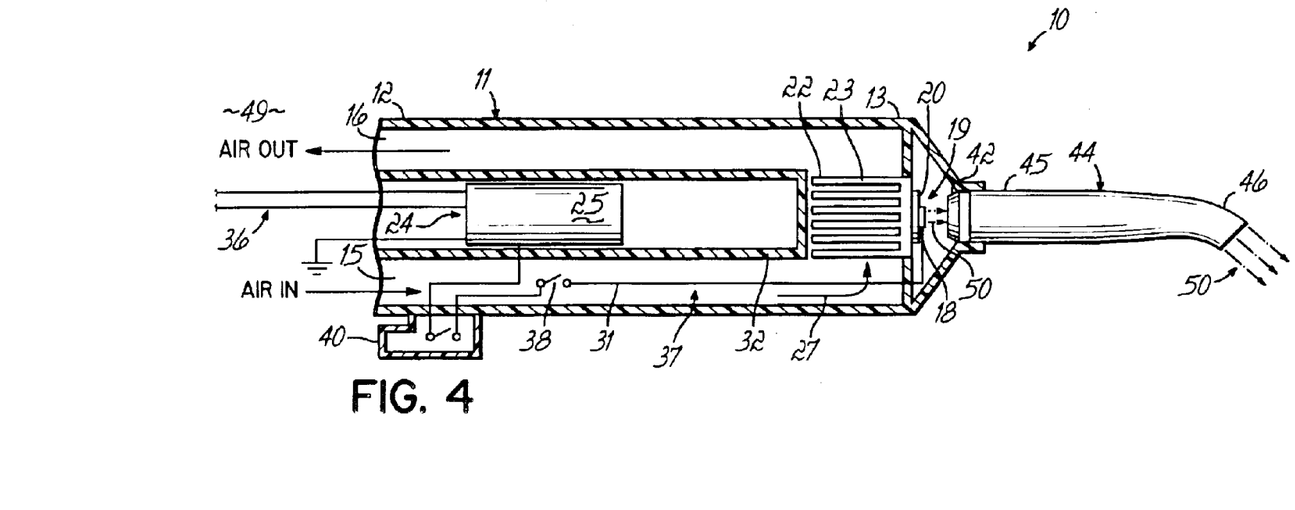
FIG. 4 is a cross-sectional view of a light-generating instrument wherein a dental chair is the source of electrical power to activate a light device and the source of air to cool the light device.

FIG. 4 illustrates an embodiment of powering the light-generating instrument 10 which may be powered electrically from a dental chair to generate light 50. Specifically, the housing 11 may be configured to provide the coupling of a source of electrical energy to power supply 25 such as by providing an electrical feed line 36 from a dental chair. As shown in the figure, electrical feed line 36 feeds electricity to a power supply 25, which, in turn, transfers the necessary electrical energy to the light device 18. The electrical feed line 36 may be a small gage, flexible conductor. Such a connection to the dental chair provides convenience and ease of use. Further, an air supply connection from the dental chair is used to operate and cool the light-generating instrument 10. The air supply connection may, for example, also include ports 68 for supplying electrical energy through an electric feed line 36 into instrument 10 (FIG. 7C). The embodiment shown in FIG. 4 also includes a housing 11 having a proximal end 12 and a distal end 13. Housing 11 also has an air inlet 15 and an air outlet 16 to allow air to flow within the housing when desired. A light device 18 is mounted to substrate 20 to emit light 50 into a light guide 44 to transmit the light 50 onto a light-curable compound. The light device 18 is cooled by heat conduction to the substrate 20 and the thermally coupled heat sink 22. The heat sink 22, in turn, is cooled by an air flow flowing into air inlet 15 and out air outlet 16 of the light-generating instrument 10.

As shown in the diagrammatic representation in FIG. 5 and exemplary embodiment in FIG. 6, the curing-light instrument 10 has an interface 47 with a dental chair 56, for operation. As shown in FIG. 6, interface 47 is a cable 52 attaching instrument 10 to dental chair 56 via individual connectors 60. Each connector 60 is suitable for interfacing the curing-light instrument 10 of the present invention with a dental chair 56. Alternatively, instrument 10 may be manufactured with a connector 60 tethered from housing 11 for interfacing with a dental chair 56 via cable 52. Similarly, dental chair 56 may comprise an interface 47 comprising a single connector 60 extending from dental chair 56. While interface 47 is represented as a cable 52, it is not so limited and may be any suitable structure capable of connecting instrument 10 to dental chair 56, or other device(s), in a dental treatment site 49.

FIGS. 7A–C illustrate exemplary embodiments of connector 60. With reference to FIG. 7A, connector 60 includes an air supply port 62 for providing air from the dental chair 56 to the air inlet 15 of instrument 10. Similarly, connector 60 includes an exhaust port 64 for receiving air circulated out of instrument 10 through air outlet 16. Typical of most dental adaptors, connector 60 also includes a water supply port 70 for providing water to the operator as needed. The embodiment illustrated in FIG. 7B further includes a light supply port 66 for transmitting light from dental chair 56 to instrument 10, such as through an optic fiber 34 illustrated in FIG. 3. Also shown is a second air supply port 72 for providing pressurized air to the operator as needed. The embodiment illustrated in FIG. 7C further includes electric supply ports 68 for providing electrical energy from the dental chair 56 directly to instrument 10, such as via the electric feed line illustrated in FIG. 4, to power instrument 10.

The invention provides a method to generate light 50 for curing light-curable compounds. The method is directed to the hardening and curing of light-curable compounds used in dental applications such as a filling, a base, a liner, or a cement type adhesive application in repairing a tooth or tooth surface. The method generally comprises providing a light device 18, which is electrically coupled to a power system 24. The power system 24 may be electrically coupled to an energy-converting device 28 in the event that the source of power is energy other than electrical energy, such as air-flow energy or visible light energy. For example, the energy-converting device 28 may convert energy from the flow of air to electrical energy, which is transferred to the power system 24 to power the light device 18. In one embodiment, the energy conversion is accomplished by a generator 29 coupled to a turbine 32, which rotates due to the air flow (FIG. 1). Alternatively, the energy-converting device 28 may convert visible light energy provided by a source of visible light 34, such as a dental chair, to electrical energy to power the light device 18 (FIG. 3). Further embodiments of the method comprise steps involving the embodiments described above. For example, one embodiment includes switching an air driven switching circuit 37, electrically coupled to the power supply 25, to power the light device 18 to emit light 50. An airflow sensor 38 is activated by air flow to trigger a switch 40 in the switching circuit 37 to activate the power system 24 to deliver power to the light device 18 (FIGS. 2 and 4).

Thus, the invention provides a small, compact light-generating instrument for use in curing light-curable compounds, preferably compounds used in dental applications such as a filling, a cement, a base, or a liner. In addition, the instrument may be used to cure compounds used as an adhesive. The invention provides convenience by powering the light-generating instrument with a power source proximate the operating unit, such as a dental chair. For example, the inventive light-generating instruments are configured to be adaptable to plug into sources of air, electricity, and light energy, provided by a dental chair, to power the instrument. The closeness of the power source to the light-generating instrument provides comfort of use and minimum hazard to the operator, patients, and other persons in the office. Furthermore, the light-generating instruments of the present invention provide added convenience by being portable units, which may easily be carried, used, and connected or disconnect from the source of power.

While the present invention has been illustrated by a description of the embodiments thereof, and while the embodiments have been described in considerable detail, it is not the intention of the applicant to restrict or in any way limit the scope of the appended claims to such detail. Additional advantages and modifications will readily appear to those skilled in the art. Therefore, the invention in its broader aspects is not limited to the specific details, representative apparatus and method, and illustrative examples shown and described. Accordingly, departures may be made from such details without departing from the spirit or scope of the present invention.

What is claimed is:

1. A light-generating instrument for curing light-curable compounds comprising:

a light device operable to emit light effective to cure a light-curable compound when supplied with electrical energy;

a cooling system operable to cool the light device when supplied with cooling fluid;

the cooling system having cooling fluid supply passages connectable to an external fluid supply for supplying fluid to the cooling system for cooling the light device;

an electrical energy supplying system operable, in response to the supply of the fluid to the cooling system, to supply electrical energy to the light device; and the electrical energy supplying system including a fluid flow sensor operable to condition the operation of the light device on the supply of cooling fluid to the cooling system.

2. The instrument of claim 1 wherein the instrument is a dental curing instrument for curing light-curable dental compounds and wherein:

the light device is operable to emit light effective to cure a light-curable dental compound when energized with electrical energy; and the cooling system has fluid supply passages connectable to air supply ports of a dental chair.

3. The instrument of claim 1 wherein the light device comprises at least one solid-state light-emitting element.

4. The instrument of claim 1 wherein the light device comprises a substrate, a plurality of solid state light-emitting diodes mounted to a substrate to form a collective array on the substrate, the array of elements operable for collectively emitting light having wavelengths within a narrow band of wavelengths effective to cure the dental compound, and a heat sink coupled to the substrate and the flow of fluid in the cooling system so as to facilitate the flow of heat generated by the light device to the cooling system.

5. The instrument of claim 1 further comprising:

an optical focusing device positioned to direct the light emitted by the light device onto a light-curable compound for curing the compound; and a light guide for transmitting light emitted from the light device onto the light-curable compound for curing the compound, the light guide comprising a plurality of fiber optic elements operably coupled together for transmitting light.

6. The instrument of claim 1 further comprising:

a housing configured to direct the air flow proximate the light device;

an airflow actuated switching circuit operable to control the supply of electrical power to the light device in response to the sensing of airflow by the airflow sensor.

7. The instrument of claim 1 wherein:

the electrical energy supplying system includes a connector connectable to an electrical energy source external to the instrument.

8. The instrument of claim 1 wherein:

the light device has a heat sink thermally coupled thereto, the heat sink consisting essentially of a liquid capable of conductively transferring heat from the light device.

9. A light-generating instrument for curing light-curable compounds comprising:

a light device operable to emit light effective to cure a light-curable compound when supplied with electrical energy;

a cooling system operable to cool the light device when supplied with cooling fluid;

the cooling system having cooling fluid supply passages connectable to an external fluid supply for supplying fluid to the cooling system for cooling the light device;

an electrical energy supplying system operable, in response to the supply of the fluid to the cooling system, to supply electrical energy to the light device; and the electrical energy supplying system including an energy converting system operable to convert non-electrical energy from external to the instrument into electrical energy.

10. The instrument of claim 9 wherein:

the energy converting system is operable to convert energy from cooling fluid flowing at the cooling system to the electrical energy.

11. The instrument of claim 9 wherein:

the energy converting system is operable to convert light from the vicinity of and external to the instrument to the electrical energy.

12. The instrument of claim 11 wherein:

the energy-converting device comprises at least one photocell to absorb light energy.

13. The instrument of claim 11 wherein:

the energy-converting device includes a light guide configured for coupling to a source of visible light energy and directing light energy to the energy-converting device.

14. A light-generating instrument for curing light-curable compounds comprising:

a light device operable to emit light effective to cure a light-curable compound when supplied with electrical energy;

a cooling system operable to cool the light device when supplied with cooling fluid;

the cooling system having cooling fluid supply passages connectable to an external fluid supply for supplying fluid to the cooling system for cooling the light device;

an electrical energy supplying system operable, in response to the supply of the fluid to the cooling system, to supply electrical energy to the light device;

the instrument being a dental curing instrument for curing light-curable dental compounds:

the light device being operable to emit light at wavelengths effective to cure a light-curable dental compound;

the cooling system having air supply lines connectable to air provided by a dental chair; and the electrical energy supplying system including:
a turbine operable to rotate in response to air flow in the cooling system, and
a generator coupled to the turbine and operable to produce electrical energy in response to rotation of the turbine.

15. A light-generating instrument for curing light-curable compounds comprising:

a light device operable to emit light effective to cure a light-curable compound when supplied with electrical energy;

a cooling system operable to cool the light device when supplied with cooling fluid;

the cooling system having cooling fluid supply passages connectable to an external fluid supply for supplying fluid to the cooling system for cooling the light device;

the cooling system being connectable to a source of air from a dental chair and further comprises an air-responsive light device actuating system;

the energy supplying system including an energy converting device to convert energy from the air flow to electrical energy and a chargeable battery to store electrical energy converted by the energy converting device; and the light device being coupled through the actuating system to the energy supplying system and operable when actuated by air flow to the actuating system to emit light onto a light-curable dental compound on a patient for curing the compound.

16. A dental curing instrument for curing light-curable dental compounds comprising:

a light device operable to emit light effective to cure a light-curable compound when supplied with electrical energy;

a cooling system operable to cool the light device when supplied with cooling fluid;

the cooling system having cooling fluid supply passages connectable to an external fluid supply for supplying fluid to the cooling system for cooling the light device;

the light device is operable to emit light effective to cure a light-curable dental compound when energized with electrical energy;

the cooling system has fluid supply passages connectable to air supply ports of a dental chair and further comprises an air-responsive light device actuating system;

the light device comprises a plurality of solid state light-emitting diodes mounted to a substrate to form a collective array on the substrate, the array of elements operable for collectively emitting light having wavelengths within a narrow band of wavelengths effective to cure the dental compound, and a heat sink coupled to the substrate and the flow of fluid in the cooling system so as to facilitate the flow of heat generated by the light device to the cooling system;

the light device has coupled thereto an optical focusing device positioned to direct the light emitted by the light device onto a light-curable compound for curing the compound and a light guide for transmitting light emitted from the light device onto the light-curable compound for curing the compound, the light guide comprising a plurality of fiber optic elements operably coupled together for transmitting light;

the light device has an electrical energy supplying system operable, in response to the supply of the fluid to the cooling system, to supply electrical energy to the light device, the electrical energy supplying system including a fluid flow sensor operable to condition the operation of the light device on the supply of cooling fluid to the cooling system, a housing configured to direct the air flow proximate the light device, and an air-flow actuated switching circuit operable to control the supply of electrical power to the light device in response to the sensing of air flow by the air-flow sensor;

the electrical energy supplying system includes an energy converting system operable to convert external energy from the dental chair into electrical energy from cooling fluid flowing at the cooling system to the electrical energy or from light from the vicinity of and external to the instrument to the electrical energy and a chargeable battery to store electrical energy converted by the power converting device; and the light device being coupled through the actuating system to the energy supplying system and operable when actuated by air flow to the actuating system to emit light onto a light-curable dental compound on a patient in the dental chair for curing the compound.

17. A method of curing light-curable compounds comprising the steps of:

providing an air flow to an energy-converting device;

converting energy from the air flow to electrical energy;

transferring the electrical energy to a power system operable to power a light device;

emitting light from the light device onto a light-curable compound for curing the compound; and supporting the energy converting system, the power system, and the light device in a housing configured to direct the airflow proximate the light device.

18. The method of claim 17 wherein the airflow providing step includes supplying air from a dental chair.

19. The method of claim 17 further comprising:

cooling the light device with the provided air; and conditioning the electrical energy powering of the light device on the availability of cooling air to the light device.

20. The method of claim 17 further comprising transmitting light emitted by the light device onto a light-curable dental compound and curing the compound thereby.

21. A method of curing light-curable dental compounds comprising the steps of:

providing a curing-light-emitting device in a hand holdable housing;

supplying cooling air from a dental chair and cooling therewith the curing-light-emitting device that includes at least one light-emitting diode;

supplying electrical energy to the curing-light-emitting device;

sensing the supplying of cooling air to the light-emitting device; and conditioning the operation of the light-emitting device on the sensed supplying of cooling air.

22. The method of claim 21 further comprising thermally coupling a heat sink to the light device to absorb heat generated by the light device while positioning the heat sink so as to be cooled by the provided air.

23. The method of claim 21 wherein the light-emitting device includes a plurality of light-emitting diodes mounted in a collective array on a substrate supported by the housing, the array operable to collectively emit light having wavelengths within a narrow band of wavelengths effective to cure light-curable dental adhesive.

24. The method of claim 21 further comprising directing the light emitted from the light device with an optical focusing device onto a light-curable compound for curing the compound.

* * * * *

UNITED STATES PATENT AND TRADEMARK OFFICE
CERTIFICATE OF CORRECTION

PATENT NO. : 6,918,762 B2 Page 1 of 1
DATED : July 19, 2005
INVENTOR(S) : Owen J. Gill and Edward Robert Shellard It is certified that error appears in the above-identified patent and that said Letters Patent is hereby corrected as shown below:

Column 12,
Line 23, reads "...light-curable dental compounds:" and should read -- ...light-curable dental compounds; --.

Signed and Sealed this

Twenty-first Day of March, 2006

JON W. DUDAS
*Director of the United States Patent and Trademark Office*